United States Patent
Morris (10) Patent No.: US 7,073,507 B2
(45) Date of Patent: Jul. 11, 2006

(54) STERILE OCULAR COVER AND METHOD

(76) Inventor: David Morris, 3204 Argyle Rd., Birmingham, AL (US) 35213

( * ) Notice: Subject to any disclaimer, the term of this patent is extended or adjusted under 35 U.S.C. 154(b) by 111 days.

(21) Appl. No.: 10/013,335

(22) Filed: Nov. 5, 2001

(65) Prior Publication Data

US 2003/0130630 A1     Jul. 10, 2003

(51) Int. Cl.
*A61B 19/00*     (2006.01)
(52) U.S. Cl. ............... 128/849; 128/852; 128/853; 128/857; 602/41; 602/42; 602/43; 602/48
(58) Field of Classification Search .......... 128/848, 128/852, 853, 854, 855, 857, 859, 869; 602/41, 602/42, 48, 64, 74, 43; 604/304–308
See application file for complete search history.

(56) References Cited

U.S. PATENT DOCUMENTS

| | | | |
|---|---|---|---|
| 3,826,253 A * | 7/1974 | Larsh et al. ............... 128/854 |
| 3,961,628 A * | 6/1976 | Arnold |
| 4,650,705 A * | 3/1987 | Ghodsian .................. 428/40.6 |
| 5,213,114 A * | 5/1993 | Bailey, Jr. .................. 128/849 |
| 5,472,436 A | 12/1995 | Fremstad .................... 604/294 |
| 5,498,478 A * | 3/1996 | Hansen et al. ............. 428/372 |
| 6,220,246 B1 | 4/2001 | Chandler et al. .......... 128/849 |

* cited by examiner

*Primary Examiner*—Henry Bennett
*Assistant Examiner*—Amanda Wieker
(74) *Attorney, Agent, or Firm*—Jones Day (57) ABSTRACT

A sterile ocular cover for an eye during surgery which includes a sheet member with a centrally located hole. The sheet member is made from a flexible material and it is designed to be placed over and in contact with the surface of the conjunctiva. The hole is slightly larger than the size of the cornea and it extends through the central portion of the sheet member.

24 Claims, 4 Drawing Sheets

STERILE OCULAR COVER AND METHOD

TECHNICAL FIELD

The field of the present invention relates generally to ocular surgical devices and procedures.

BACKGROUND OF THE INVENTION

Generally, surgery is performed in a sterile operating field. A sterile operating field is an area of the body that has been cleansed, with a surgical detergent and/or an antiseptic, to reduce or eliminate any surface bacteria that may be found on the body surface in and around the area of the planned surgical incision. Since this cleansing cannot completely eliminate all surface bacteria, the operating field is then covered with a sterile cover through which the incision is made, thus extending the sterile operating field up to the area of incision. The sterile cover, also referred to as a sterile drape, prevents any contact between the sterilized surgical instruments and the surface of the body. By preventing such contact, the sterile cover reduces the possibility that any remaining surface bacteria will attach to a sterile surgical instrument and be transported into the area of incision.

The unique structure of the eye, however, has made it generally difficult for surgeons to establish and maintain a sterile operating field up to the area of incision near the cornea, which has a general diameter between 11–12 mm in normal patient populations. The difficulty exists because the surgeon routinely makes an incision near or through the conjunctiva, the moist and transparent membrane that covers exposed surfaces of the eye and the eyelids, and the conjunctiva generally contains high levels of surface bacteria. Thus, the surface of the eye is the only portion of the body surface that does not allow the intense application of surgical detergents or antiseptics, due to its delicate nature, nor the application of an adherent sterile drape, as is used on the skin, due to its moist character.

Figure 1:
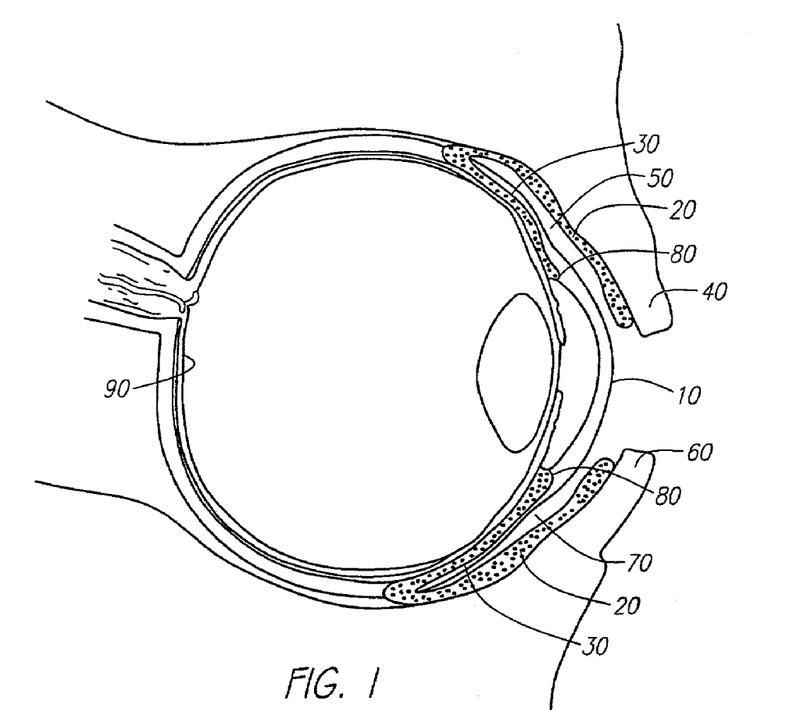
FIG. 1 is a cross section view of the anatomy of the eye.

In cross section (FIG. 1), the anatomy of the eye contains a surface membrane, the conjunctiva, which extends from the inner eyelid margin to the edge of the cornea 10. Where the conjunctiva covers the inner surface of the eyelid, it is referred to as the palpebral conjunctiva 20. Where the conjunctiva covers the white wall of the eye (the sclera), it is referred to as the bulbar conjunctiva 30. The space between the upper eyelid 40 and the bulbar conjunctiva 30 is referred to as the upper fornix 50 and the space between the lower eyelid 60 and the bulbar conjunctiva 30 is referred to as the lower fornix 70. The region of the eye where the bulbar conjunctiva 30 terminates into the cornea 10 is referred to as the limbus 80. The light sensitive film lining the back two-thirds of the eye is the retina 90.

Figure 2:
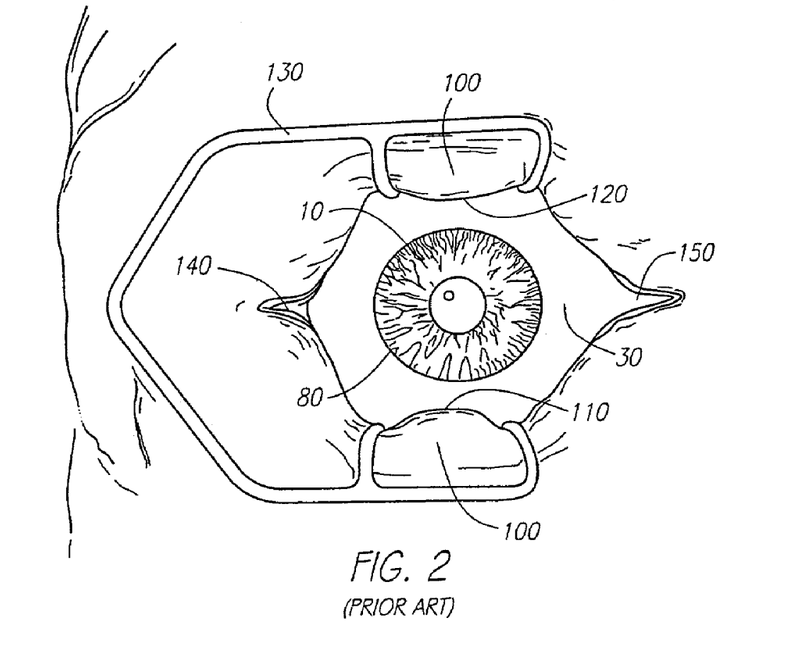
FIG. 2 is a top view of the eye when the eye has been prepared for a surgical procedure using existing sterile draping techniques.
Figure 3:
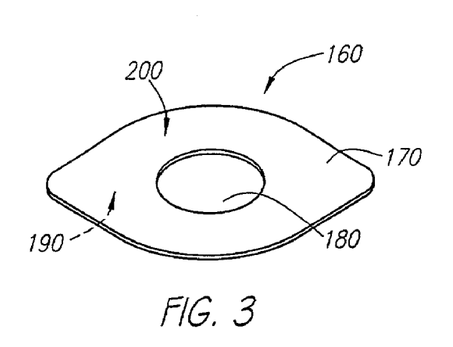
FIG. 3 is a perspective view of a sterile ocular cover.

Currently, the ocular surgeon uses a translucent sterile drape 100 that covers the operating field extending only up to the margins of the lower eyelid 110 and the upper eyelid 120, where it is folded over the eyelid margins, into the fornices, by the speculum 130 that also holds open the eyelids (FIG. 2). M. G. Speaker & J. A. Menikoff, Int. Ophthalmology Clinic, 33: 51–70 (1993). This form of draping, however, does not establish a sterile field beyond the margin of the eyelids 110, 120 and the margins of both the lateral canthus 140 and medial canthus 150. During ocular surgery, the surgeon typically makes an eyewall incision through the cornea 10 or the bulbar conjunctiva surface 30, well beyond the margin of the sterile drape 100, near the limbus 80 (FIG. 2). Consequently, there is a continued concern that a patient undergoing eye surgery, such as cataract extraction, may be at an increased risk to develop a post operative infection that may develop from the introduction of conjunctival surface bacteria into the site of the incision.

In eye surgery, post-operative infection of the interior of the eye is called endophthalmitis. Despite current preventative efforts, endophthalmitis occurs in approximately 1 in 1000 ocular surgical procedures and is the most feared of all postoperative complications. J. C. Javitt, S. Vitale, J. K. Canner, et al., *Arch Ophthalmology*, 109:1085–1089 (1991). The bacteria that cause this complication closely coincide with the typical bacteria that have been proven to reside on the conjunctival surface of the eye. In fact, genetic studies have frequently shown that the infecting organism in endophthalmitis is identical with the bacteria cultured from the conjunctival surface of the same eye. M. G. Speaker, F. A. Milch, M. K. Shah, et al., *Ophthalmology*, 98: 639–650 (1991).

During a typical ocular surgical procedure, surgical instruments, irrigation fluids, and intraocular implant lenses commonly contact the exposed bulbar conjunctiva. This contact often results in the transportation of conjunctival surface bacteria into the interior of the eye, F. M. Wilson, *Int. Ophthalmology Clinic*, 27: 97–108 (1987), sometimes resulting in a case of endophthalmitis. Surgical statistics indicate that between 26–43% of cataract extraction patients develop culture positive aqueous fluid that results from surface conjunctival bacteria that have been transported into the eye during surgery. M. G. Speaker & J. A. Menikoff, *Int. Ophthalmology Clinic*, 33: 51–70 (1993).

When a patient suffers from endophthalmitis, the affected eye is temporarily blinded, and there is great concern that the infection will permanently destroy or impair the patient's vision, so it is generally considered an emergency. As such, the patient may be treated with intraocular antibiotic therapy and surgical debridement. This course of therapy, however, does not always restore the patient's vision. In fact, one half of the eyes that are afflicted with endophthalmitis remain legally blind after surgery, and one out of ten is removed, shrinks, or becomes cosmetically objectionable. A. J. Kanellopoulos & F. B. Dreyer, *Int. Ophthalmology Clinic*, 36 (2): 97–108 (1996).

Extensive efforts have been made over the last 30 years to reduce the amount of bacteria on the surface of the conjunctiva by optimally treating the exposed conjunctiva topically with preoperative and postoperative antibiotic eye drops, and intraoperatively with subconjunctival antibiotic injection. D. C. Classen, R. S. Evans, S. L. Pestontnik, et al., *New England Journal of Medicine*, 326: 281–286, (1992); M. B. Starr & J. M. Lally, *Survey of Ophthalmology*, 39 (6): 485–501 (1995). These approaches, however, have not been completely effective in the prevention of post surgical infections. Antibiotic eye drops are cumbersome to apply in a sufficient amount to reduce conjunctival bacterial colony counts to acceptable levels. Additionally, the use of antibiotic eye drops is expensive; requires patient compliance; and exposes the patient to potential complications associated with adverse or toxic reactions. Furthermore, there is a concern that the overuse of antibiotics in prophylaxis contributes to the emergence of resistant bacterial strains that are difficult to eradicate. Finally, sub-conjunctival injections have been reported to accidentally pierce the eye wall itself, instantly destroying all central vision by chemically injuring the retina (see FIG. 1). P. A. Campochiaro & B. P. Conway, *Arch Ophthalmology*, 109: 946–950, (1991).

Because the concern over the development of endophthalmitis is great, and the antibiotic approaches have not been completely successful, ocular surgeons have attempted to additionally reduce conjunctival surface bacteria by using antiseptics. Unfortunately, the use of antiseptics has been limited because the ocular surface is delicate. Thus, the use of antiseptic preparation must be limited both in strength and duration to avoid toxicity. Of the potential antiseptic agents, Povidine Iodine 5% has been shown to be well tolerated and to have an additional effect to topical antibiotics in endophthalmitis prevention. M. G. Speaker & J. A. Menikoff, *Ophthalmology*, 98: 1769–1775 (1991). This effectiveness, however, is proportional to the amount of time the solution stays in contact with the surface of the conjunctiva. Thus, the use of Povidine Iodine 5% has not been completely effective, partly because it is not left on the surface of the eye for prolonged periods due to toxicity.

In addition to the potential risks associated with endophthalmitis caused by surface bacteria, complications associated with phototoxicity can also result from an ocular surgical procedure. When ocular surgery is performed, the surgeon must use a surgical microscope that requires high-powered illumination. This illumination, in the form of intense light, can damage the retina. Such damage to the retinal tissues is referred to as phototoxicity or photic retinopathy.

Although such advanced technology has vastly improved the precision of ocular surgery, the use of modern microscopes in eye surgery can paradoxically damage the retina when used without precautions. For optimal surgical viewing, the surgical microscope emits light to illuminate the surgical field. Some of this light is reflected off the conjunctiva and the sclera, and the rest is transmitted through the clear cornea to the retina. During eye surgery, the patient's natural defenses against this light are disabled. Consequently, the patient is especially vulnerable to phototoxicity of the retina.

The damaging effect of medical instrument illumination has been recognized for three decades. In 1973, Tso described photic retinopathy lesions that were intentionally produced in the eyes of a monkey. M. Tso, *Investigative Ophthalmology* 12: 17–34 (1973). Later, McDonald and Irvine described a group of patients after cataract extraction that had similar lesions. H. R. McDonald & A. R. Irvine, *Ophthalmology* 90: 945–951 (1983). Such lesions have also been intentionally demonstrated by experiments that exposed human eyes, prior to the removal of the eye for an unrelated malignant tumor, to an operating microscope light for sixty minutes. W. R. Green W R & D. M. Robertson, *American Journal of Ophthalmology*, 112: 520–527 (1991).

The prevalence rate of retinal phototoxicity has been estimated to range from 3% to 7.4% after surgery for cataract extraction using the illuminated microscope. S. G. Khwarg, F. A. Linstone, S. A. Daniels, et al., *American Journal of Ophthalmology*, 103: 255–263 (1987); J. E. Gomolin & R. K. Koehekoop, *Canadian Journal of Ophthalmology*, 28: 221–224 (1993). Even if a characteristic retinal burn is not present, it has been postulated that subtle, chronic cystoid edema may be caused at the visual focal point of the macula. At its worst, phototoxicity can produce permanent legal blindness in the effected eye.

Protection of the human retina against phototoxicity is partly provided by the ocular media, which filters or absorbs the most damaging ultra-violet rays. The pupil is also capable of constricting in response to bright light, thus reducing light transmission to the retina by more than 80%. R. E. Records & J. L. Brown, *Adaptation in Duane's Foundations of Clinical Ophthalmoloay*, vol. 2, ch. 16, Tasmas and Jaeger Editors (1991). Finally, if light is too intense, the eyelids will close, or the brain may turn the gaze of the eyes away from the offending light source.

During eye surgery, almost all of these retinal protective mechanisms may be disabled. The pupil is usually paralyzed pharmacologically in the dilated state. The human lens is often removed, allowing greater transmission of potentially damaging light to the retina. An eyelid retractor (speculum) is employed to prevent eyelid closure. Under these circumstances, a typical operating microscope on high illumination can produce a visible photic retinopathy lesion in 4 to 7.5 minutes. A. R. Irvine, I. Wood, & B. W. Morris, *Trans-American Ophthalmological Society*, 82: 239–260 (1984).

For over twenty years, various efforts have been made to understand and prevent phototoxicity during eye surgery. W. A. Solley & P. Sternberg, *Int. Ophthalmology Clinic*, 39 (2): 1–12 (1999). The filtering of shorter wavelength light lessens but does not eliminate retinal damage. R. H. Keates & P. R. Armstrong, *Ophthalmic Surgery*, 16: 40–41 (1985). Similarly, the filtering of infrared light greater than 700 nanometers is only partially helpful. M. A. Mainster, W. T. Ham, F. C. Dehori, *Ophthalmology*. 90: 927–932 (1983). The avoidance of intense illumination has been recommended as has tilting the microscope to avoid the macula. Defocusing the beam on the retina, by placement of an air bubble in the anterior chamber, does not prevent phototoxicity. The use of corneal covers and eclipse filters has been advocated, but these devices obscure the operating field and can be used only during pauses in surgery. Finally, even proximity devices have been advocated which will turn the microscope light off when the surgeon's head leaves the microscope during pauses in eye surgery. E. Urinkowsky, M. Cahane, I. Ashkenanazi, M. Blumenthal, & I. Avni, *Ophthalmic Surgery*, 25 (2): 122–5 (1994).

SUMMARY OF THE INVENTION

The present invention is directed to a sterile ocular cover for the protection of an eye during surgery. The sterile ocular cover includes a sheet member made from a flexible material with a hole extending through the central portion thereof.

In a first separate aspect of the present invention, the cover is sized to be placed over and in contact with the surface of the conjunctiva of the eye. The hole is sized slightly larger than the diameter of the cornea.

In a second separate aspect of the present invention, the ocular cover may include a flap in the hole that is equal in extent to the hole. The flap would be attached at its periphery to the periphery of the hole.

In a third separate aspect of the present invention, the ocular cover is contemplated to include the sheet member being made of opaque material.

In a fourth separate aspect of the present invention, the ocular cover is contemplated to include the sheet member being made of absorbent material.

In a fifth separate aspect of the present invention, the fourth separate aspect may be further contemplated to include a sheet member impregnated with an antibiotic or an antiseptic.

In a sixth separate aspect of the invention, the sterile ocular cover includes the sheet member defining a body and a wicking portion. The body has the centrally located hole, the hole is sized to be no more than about 6 mm in diameter larger than the cornea. The sheet member also has a wicking portion that can be positioned over a lateral canthus of an eye.

In a seventh separate aspect of the invention, the sixth separate aspect of the invention is further contemplated to include a flap in the hole that is equal in extent to the hole. The flap being attached at its periphery to the periphery of the hole.

In a eighth separate aspect of the invention, the seventh separate aspect of the invention is further contemplated to include a sheet member impregnated with an antibiotic or an antiseptic.

In an ninth separate aspect of the present invention, the sixth separate aspect of the invention is further contemplated to include a handle that extends beyond the canthus of an eye.

In an tenth separate aspect of the present invention, a surgical method includes placing a sterile ocular cover over the conjunctiva and performing an ocular surgery with the conjunctiva covered.

In an eleventh separate aspect of the invention, a treatment method includes placing a sterile ocular cover impregnated with an antibacterial solution over the conjunctiva of the eye and removing the impregnated cover before performing ocular procedure.

In a twelfth separate aspect of the invention, combinations for increased advantage of any of the foregoing aspects and features are contemplated.

Accordingly, it is an object of the present invention to provide improved sterile ocular procedures and devices therefor.

DETAILED DESCRIPTION OF THE PREFERRED EMBODIMENTS

The preferred embodiments will now be described with reference to the drawings. To facilitate description, element numerals designating an element in one figure will represent the same element in any other figure.

Turning to FIGS. 3–6, a sterile ocular cover 160 is shown including a sheet member 170 with a centrally located hole 180. The hole 180 extends through the sheet member 170 between an inner surface 190 and an outer surface 200. The sheet member 170 is sized for the placement over and in contact with the exposed surface of the bulbar conjunctiva. The shape of the sheet member 170 is generally ovoid. The ovoid shape includes two tapered ends that extend away from the wider central region of the sheet member 170. When the sheet member 170 of the ocular cover 160 is placed on the eye, the sheet member 170 extends horizontally from the medial canthus to the lateral canthus and vertically from the upper fornix to the lower fornix.

The hole 180 is centrally located in the sheet member 170 and the shape of the hole 180 is circular. Generally, the hole 180 is advantageously sized to be slightly larger than the diameter of the cornea. The circular diameter of the hole 180 is no more than about 6 mm larger in diameter than the diameter of the cornea, which is generally 11–12 mm. The size of the hole 180 affords the surgeon an unimpeded view of the central corneal region when the sheet member 170 is placed over the surface of the exposed conjunctiva. The size of the hole 180 also provides a small border region around the cornea that is not covered by the sheet member 170. When ocular surgeons perform intraocular procedures, they usually make incisions within the 3 mm area immediately adjacent to the perimeter of the cornea called the limbus. Because the hole 180 is configured to provide access to this region, the surgeon can make these incisions and perform other surgical manipulations without removing the ocular cover 160.

In the preferred embodiment, the sheet member 170 is a single piece molded product. Generally, the sheet member 170 can be made from a medical grade material that is both opaque and flexible. Examples of such materials include Gelfoam, Silicone, Myracel, or Collagen, but other appropriate materials are contemplated.

In operation, as shown in FIGS. 9–12, the ocular cover 160 protects the ocular surgical patient by creating a sterile physical barrier over the exposed surface of the bulbar conjunctiva. When the sheet member 170 is positioned over the exposed surface of the bulbar conjunctiva, the sheet member 170 extends a sterile physical barrier horizontally from the medial canthus to the lateral canthus and vertically from the inferior fornix to the superior fornix. This layer of sterile protection prevents a surgical instrument from making contact with the exposed conjunctiva. As the surgeon performs a surgical procedure without the cover, surgical instruments typically make contact with the exposed surface of the bulbar conjunctiva. This contact may deposit conjunctival bacteria on the surface of the sterile surgical instrument. The sheet member 170 provides a sterile outer surface 200 that prevents the surgical instrument from making direct contact with the exposed surface of the bulbar conjunctiva. This prevents any remaining conjunctival bacteria from attaching to the surgical instrument. Thus, the ocular cover 160 advantageously prevents the attachment of conjunctival bacteria to the sterile surgical instrument and thereby prevents the transportation of such bacteria into the eye.

The placement of the sheet member 170 under the edge of the margin of the eyelid advantageously maintains the position of the ocular cover 160 during surgery. When the sheet member 170 is placed on the eye, the surgeon positions the sheet member 170 to extend under and beyond the margin of the eyelids into the fornices of the eye. In this position, the eyelids, which are covered by a sterile drape, come in direct contact with the outer surface 200 of the sheet member 170. This contact generates downward force on the sheet member 170 that maintains the position of the ocular cover 160 on the surface of the eye. Thus, the surgeon can perform surgery with the ocular cover 160 on the eye and the cover remain relatively immobile during the surgical procedure.

The ocular cover 160 also provides a physical barrier that prevents light waves from reflecting off the highly reflective, wet surface of the exposed bulbar conjunctiva or the underlying white sclera. When the sheet member 170 is placed over and in contact with the conjunctiva, the sheet member 170 prevents light waves from reflecting off the surface of the bulbar conjunctiva or sclera. The elimination of the reflected light waves results in an overall reduction in the brightness of the microscope illuminated field. This reduction in of the microscope illuminated field brightness has a direct impact on the vision of the surgeon. As the opaque, darkly colored ocular cover 160 prevents the reflection of light waves off of the conjunctiva and scleral surfaces, the brightness of the microscope illuminated field is reduced to only the light reflected from the intended operating field of the cornea. As the surgeon's eye's light sensitivity increases through normal visual light adaptation, possibly by a factor of one hundred or greater, the surgeon is able to maintain the necessary visual acuity of the operating field while simultaneously using substantially less intense microscope illumination. R. E. Records & J. L. Brown, *Adaptation in Duane's Foundations of Clinical Ophthalmology*, vol. 2, ch. 16, Tasmas and Jaeger Editors (1991). Phototoxicity of the retina is directly dependent on two factors—the intensity of the illumination and the length of time that the retina is exposed to the illumination. The greater the intensity of the light used, the more likely that the patient may suffer phototoxicity. Similarly, the longer a patient is exposed to direct retinal illumination, the more likely the patient will develop phototoxicity. The use of the ocular cover 160 provides benefits related to both of these factors. As the ocular cover 160 maintains the darker microscope illuminated field, the surgeon can reduce the intensity of the operative field illumination during surgery because of his improved dark adaptation. This reduces the chance that the patient will suffer phototoxicity from exposure to high intensity light. Additionally, The reduction in illumination intensity also increases the amount of time the retina can be exposed to the direct illumination without suffering phototoxicity. This provides the surgeon with more time to complete the surgical procedure.

In another embodiment, the sheet member 170 can be made from an opaque and flexible material that is also absorbent and generally hydrophilic. In this configuration, the sheet member 170 can absorb surgical solutions such as antibiotics and antiseptics. Both of these solutions can be used to aid in the reduction of surface bacteria before and during the surgical procedure. In use, the absorbent sheet member 170 can be impregnated with a solution of Povidine Iodine 5% and positioned over the exposed surface of the conjunctiva. In this procedure, the sheet member 170 advantageously reduces surface bacteria by establishing and maintaining contact between the surface of the eye and the Povidine Iodine 5% contained in the sheet member 170 for so long as it is employed preoperatively or intraoperatively.

The absorbent sheet member 170 can also be used to deliver antibiotic solutions to the surface of the eye prior to or during surgery. In this procedure, the absorbent sheet member 170 can be immersed in or impregnated with an antibiotic solution before the surgical procedure. Examples of contemplated antibiotics include the antibiotics belonging to the cephalosporin and aminoglycoside families. After immersion in the antibiotic solution, the absorbent sheet member 170 can be positioned over the exposed surface of the conjunctiva. The ocular cover 160 can then be removed from the eye before surgery or left in the eye during the surgical procedure. In operation, the sheet member 170 that is impregnated with antibiotics maintains the surface antibiotic levels before and/or during the surgical procedure by keeping the absorbed antibiotic solution directly in contact with the surface of the conjunctiva. Additionally, the absorbent sheet member 170 can be impregnated with an ocular surface lubricant, cyclogel 1% for pupil dilation, or another pharmaceutical agent. Thus, the absorbent sheet member can serve as a delivery vehicle providing solutions of pharmaceutical agents to the surface of the eye.

Figure 4:
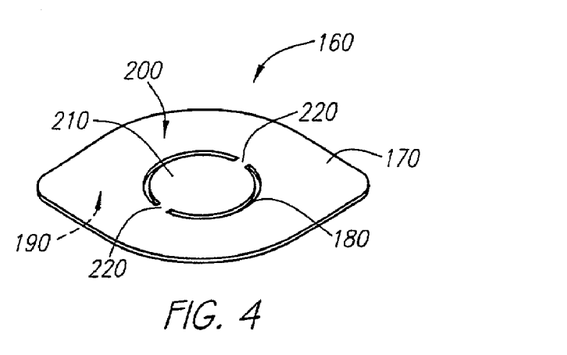
FIG. 4 is a perspective view of a sterile ocular cover with a flap attached to the hole.
Figure 5:
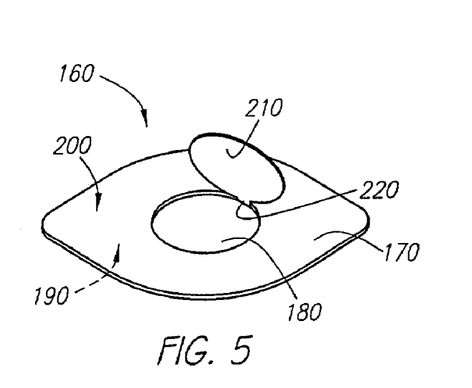
FIG. 5 is a perspective view of a sterile ocular cover with a flap positioned outside the hole.
Figure 6:
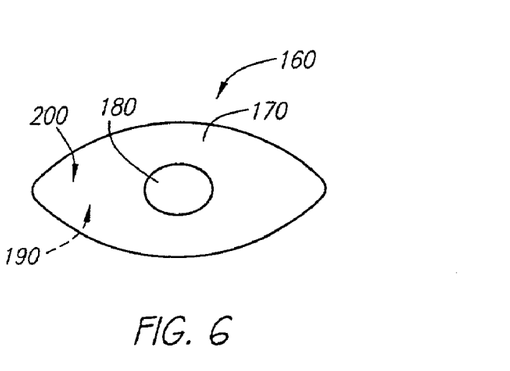
FIG. 6 is a top view of the sterile ocular cover of FIG. 3.

In another embodiment, as shown in FIGS. 4 and 5, the sterile ocular cover 160 of the preferred embodiment further includes a flap 210. The flap 210 is shaped in equal extent to the hole 180. As seen in FIG. 4, the flap 210 is attached at its periphery to the periphery of the hole 180 by two tabs 220. The tabs 220 are located parallel to the longitudinal axis of the sheet member 170 directly opposite each other. The flap 210 is advantageously designed to allow the user to intermittently moisten the surface of the cornea while still permitting surgical access to the cornea and the region of the sclera adjacent to the cornea, when the flap is retracted.

In use, the flap 210, as shown in FIG. 5, may be severed at one of the tabs 220 thereby transforming the other connected tab 220 into a living hinge. Before the insertion of the sheet member 170 onto the eye, the surgeon can cut one of the tabs 220 thereby making the flap 210 separable and allowing the hole 180 to be completely exposed. When a tab 220 is severed, the flap 210 can be positioned outside the hole 180 by moving the flap 210 to a position adjacent to the hole 180. This position allows the surgeon to perform the surgical procedure with direct access to the cornea and the region adjacent to the cornea. The flap 210 may also be positioned inside the hole 180 whereby the flap 210 is designed to provide moisture to the surface of the cornea when the surgeon does not require access to the cornea. Further, the flap 210 can be positioned over the cornea to prevent the penetration of light through the cornea to protect the retina from phototoxicity.

Figure 7:
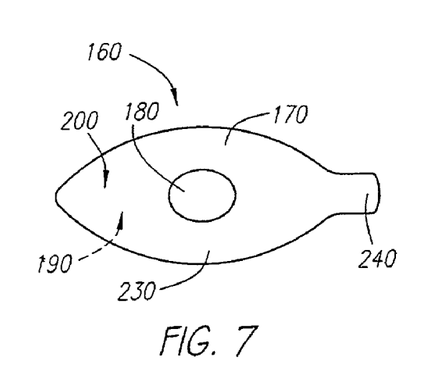
FIG. 7 is a top view of the sterile ocular cover of FIG. 3 with a wicking portion.

In another embodiment, as shown in FIG. 7, the ocular cover 160 includes a sheet member 170 that includes a body 230 with a hole 180 centrally therethrough, and a wicking portion 240. The body 230 is sized for the placement over and in contact with the exposed surface of the bulbar conjunctiva. Generally, the shape of the body 230 is ovoid having two tapered ends. In this design, the tapered ends have different configurations. The first end is tapered to cover the exposed surface of the conjunctiva and extends away from the body toward the medial canthus. The second end extends away from the body laterally and terminates into the wicking portion 240. The wicking portion 240 is rectangularly shaped and extends away from the body 230 in the same plane beyond the surface of the lateral canthus. The hole 180 extends between the inner surface 190 and an outer surface 200 of the body 230. The shape of the hole 180 is preferably round, but it can also exist in other configurations to accommodate scleral entry. The hole 180 sized to be no more than about 6mm in diameter larger than the diameter of the cornea. This size allows the surgeon to maintain the sterile operating field beyond the eyelids while simultaneously performing surgical procedures in the scleral region adjacent to the cornea.

As shown in FIG. 7 the sheet member 170 includes a wicking portion 240. The wicking portion 240 is advantageously designed to wick excess fluid from the surface of the eye during surgery reducing the chance that pooled fluid will enter the incision, transporting bacteria from the conjunctiva into the eye. When the sheet member 170 is placed on the eye, the body 230 is positioned over the exposed surface of the bulbar conjunctiva and the wicking portion 240 is positioned over the lateral canthus. As fluids are supplied to the eye, they can accumulate in the lateral perimeter of the surface of the eye. The wicking portion 240 removes these excess fluids by absorbing them into the material of the sheet member 170 located in the wicking portion 240.

Figure 8:
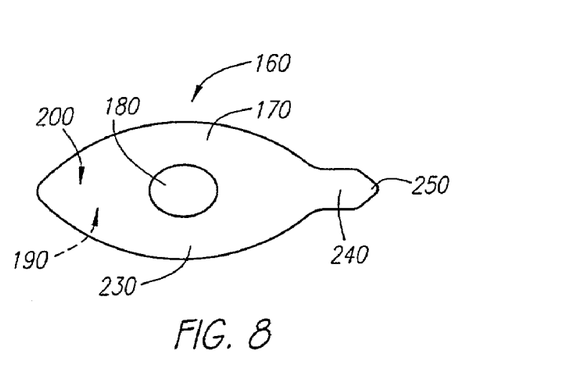
FIG. 8 is a top view of the sterile ocular cover of FIG. 3 with a wicking portion and a handle.
Figure 9:
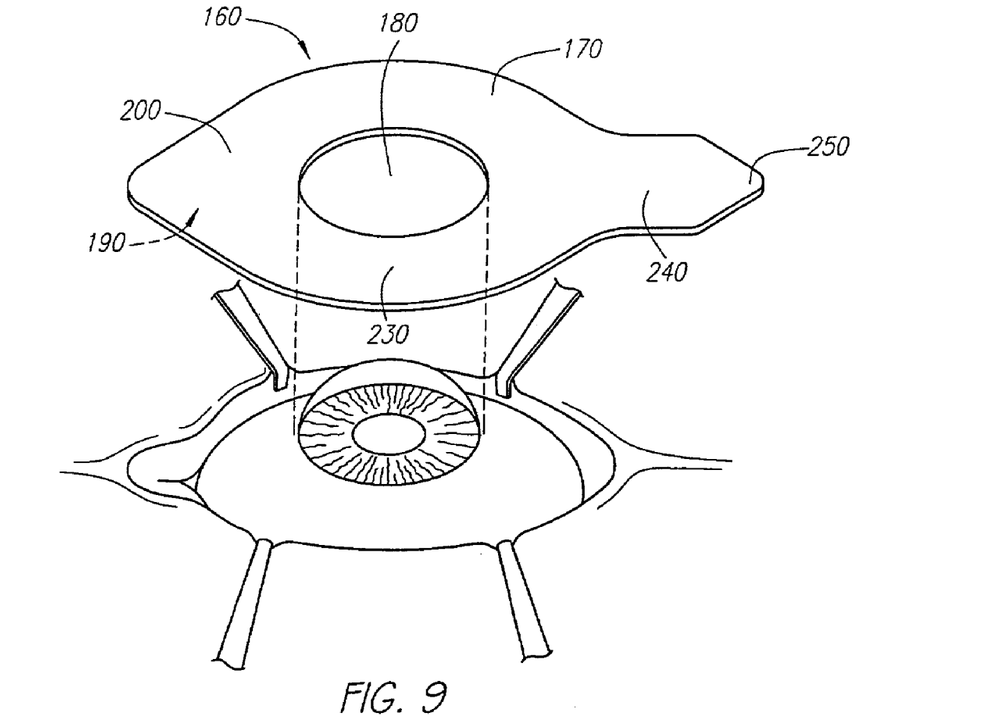
FIG. 9 is a perspective view of the eye after preparation for surgery and the sterile ocular cover before the sterile ocular cover has been placed on the eye.
Figure 10:
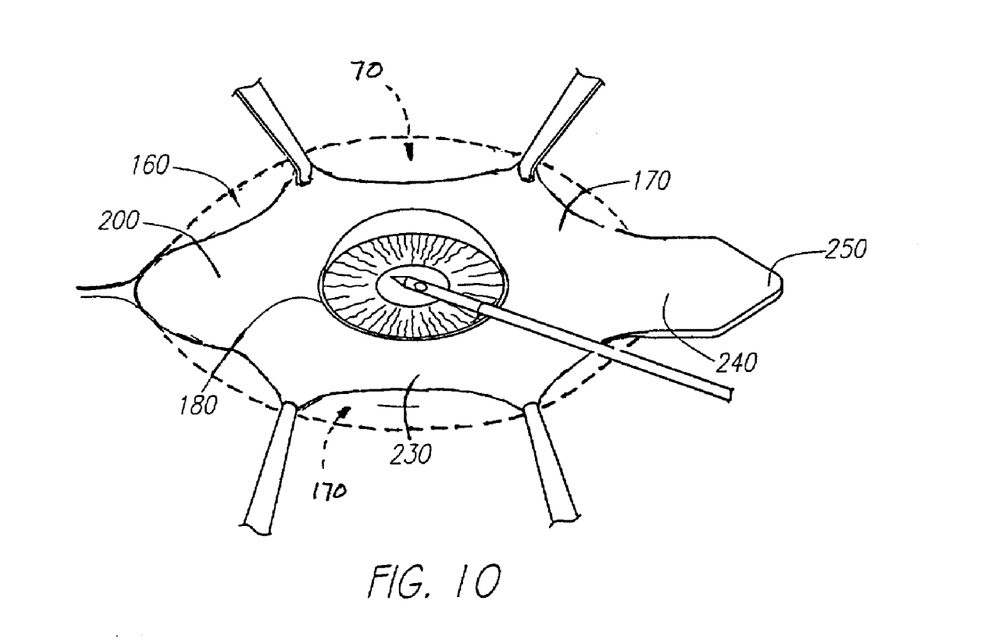
FIG. 10 is a perspective view of the eye during a surgical procedure with the sterile ocular cover placed on the eye and a surgical procedure being performed in the area adjacent to the cornea.
Figure 11:
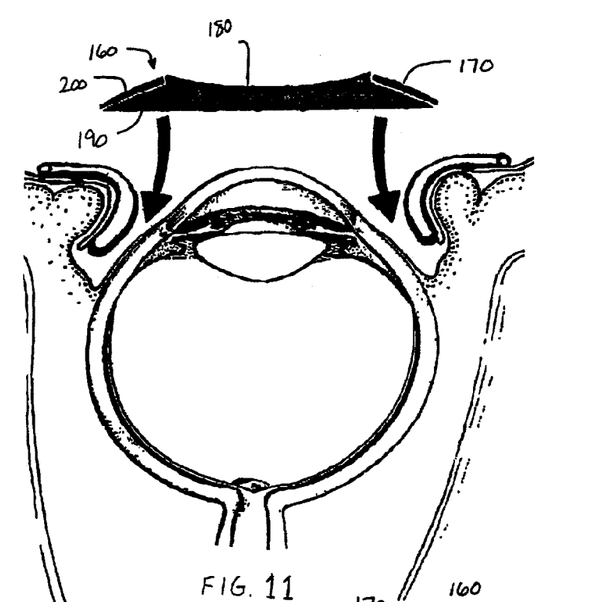
FIG. 11 is a cross section view of the eye and the sterile ocular cover before the sterile ocular cover has been placed on the eye.
Figure 12:
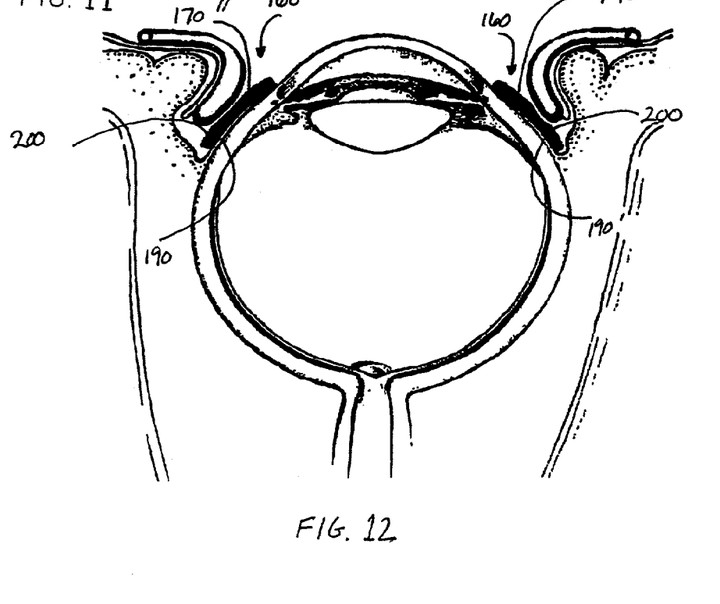
FIG. 12 is a cross section view of the eye and the sterile ocular cover with the sterile ocular cover placed on the conjunctiva of the eye.

In another embodiment, as shown in FIG. 8, the sterile ocular cover 160 further includes a handle 250. The handle 250 is attached to the terminal end of the wicking portion 240 and extends away from the wicking portion 240 in the same plane. The handle is shaped in an elongate configuration that advantageously allows the user to grasp the handle 250 and place the ocular cover 160 into the exposed surface of the eye. In use, the handle 250 serves as a place for adjusting the position of the body 230 and the wicking portion 240 during surgery. The user can move the ocular cover 160 by grasping the handle 250 and positioning the ocular cover 160 to the necessary location.

Thus, the improved sterile ocular procedures and devices are disclosed. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. A sterile ocular cover for an eye during surgery, comprising
a sheet member including a body sized for placement over and in contact with the surface of the conjunctiva of the eye, and a wicking portion, the sheet member being made of a flexible and absorbent material, the body including a hole therethrough, the hole being a diameter of 11–12 mm plus no more than about 6 mm larger than the hole diameter, the wicking portion extending outwardly from the body and being positionable over and in contact with a lateral canthus of the eye.

2. The ocular cover of claim 1, wherein a flap is constructed equal in extent to the hole and attached at the periphery of the flap to the periphery of the hole.

3. The ocular cover of claim 1, wherein the sheet member is constructed from an opaque material.

4. The ocular cover of claim 1, wherein the sheet member is impregnated with an antiseptic.

5. The ocular cover of claim 1, wherein the sheet member is impregnated with an antibiotic.

6. A sterile ocular cover for an eye during surgery, comprising
a sheet member including a body sized for placement over and in contact with the surface of the conjunctiva of the eye, a wicking portion, and a handle, the sheet member being made of a flexible and absorbent material, the body including a hole therethrough, the hole being a diameter of 11–12 mm plus no more than about 6 mm larger than the hole diameter, the wicking portion extending outwardly from the body and being positionable over and in contact with a lateral canthus of the eye, the handle extending outwardly from the body and being positionable beyond the canthus of the eye.

7. The ocular cover of claim 6 further comprising
a flap equal in extent to the hole and attached at the periphery of the flap to the periphery of the hole.

8. The ocular cover of claim 6, wherein the sheet member is constructed from an opaque material.

9. The ocular cover of claim 6, wherein the sheet member is impregnated with an antiseptic.

10. The ocular cover of claim 6, wherein the sheet member is impregnated with an antibiotic.

11. A treatment method comprising the steps of
impregnating an ocular cover having a wicking member and constructed from an opaque material with an antibacterial solution,
placing the impregnated ocular cover over a conjunctiva of an eye, and
removing the impregnated cover from the eye before performing an ocular procedure.

12. The treatment method of claim 11, wherein the sterile cover is impregnated with an antiseptic.

13. The treatment method of claim 11, wherein the sterile cover is impregnated with an antibiotic.

14. An ocular cover for an eye during surgery, comprising
a sterile, flexible sheet member of generally ovoid shape sized such that when constructed it is congruous with the conjunctiva surface of an eye, extending from the medial canthus to the lateral canthus and from the upper fornix to the lower fornix;
a circular hole in the center of said sheet member having a diameter larger than the cornea surface diameter of an eye, but not more than about 11–12 mm plus no more than about 6 mm larger than the hole diameter and wherein said sheet member is absorbent.

15. The ocular cover of claim 14 wherein said sheet member is impregnated with an antiseptic.

16. The ocular cover of claim 14 wherein said sheet member is impregnated with an antibiotic.

17. A sterile ocular cover for an eye during surgery, comprising
a sheet member including a body sized for placement over and in contact with the surface of the conjunctiva of the eye, a wicking portion, and a flap, the sheet member being made of a flexible and absorbent material, the body including a hole therethrough, the hole being a diameter of 11–12 mm plus no more than about 6 mm larger than the hole diameter, the wicking portion extending outwardly from the body and being positionable over and in contact with a lateral canthus of the eye; the flap is constructed equal in extent to the hole and attached at the periphery of the flap to the periphery of the hole.

18. A sterile ocular cover for an eye during surgery, comprising
a sheet member including a body sized for placement over and in contact with the surface of the conjunctiva of the eye, and a wicking portion, the sheet member being made of a flexible and absorbent material, the body including a hole therethrough, the hole being a diameter of 11–12 mm plus no more than about 6 mm larger than the hole diameter, the wicking portion extending outwardly from the body and being positionable over and in contact with a lateral canthus of the eye; wherein the sheet member is constructed from an opaque material.

19. A sterile ocular cover for an eye during surgery, comprising
a sheet member including a body sized for placement over and in contact with the surface of the conjunctiva of the eye, and a wicking portion, the sheet member being made of a flexible and absorbent material, the body including a hole therethrough, the hole being a diameter of 11–12 mm plus no more than about 6 mm larger than the hole diameter, the wicking portion extending outwardly from the body and being positionable over and in contact with a lateral canthus of the eye; wherein the sheet member is impregnated with an antiseptic.

20. A sterile ocular cover for an eye during surgery, comprising a sheet member including a body sized for placement over and in contact with the surface of the conjunctiva of the eye, and a wicking portion, the sheet member being made of a flexible and absorbent material, the body including a hole therethrough, the hole being a diameter of 11–12 mm plus no more than about 6 mm larger than the hole diameter, the wicking portion extending outwardly from the body and being positionable over and in contact with a lateral canthus of the eye; wherein the sheet member is impregnated with an antibiotic.

21. A sterile ocular cover for an eye during surgery, comprising a sheet member including a body sized for placement over and in contact with the surface of the conjunctiva of the eye, a wicking portion, a handle, and a flap, the sheet member being made of a flexible and absorbent material, the body including a hole therethrough, the hole being a diameter of 11–12 mm plus no more than about 6 mm larger than the hole diameter, the wicking portion extending outwardly from the body and being positionable over and in contact with a lateral canthus of the eye, the handle extending outwardly from the body and being positionable beyond the canthus of the eye, the flap equal in extent to the hole and attached at the periphery of the flap to the periphery of the hole.

22. A sterile ocular cover for an eye during surgery, comprising a sheet member including a body sized for placement over and in contact with the surface of the conjunctiva of the eye, a wicking portion, and a handle, the sheet member being made of a flexible and absorbent material, the body including a hole therethrough, the hole being a diameter of 11–12 mm plus no more than about 6 mm larger than the hole diameter, the wicking portion extending outwardly from the body and being positionable over and in contact with a lateral canthus of the eye, the handle extending outwardly from the body and being positionable beyond the canthus of the eye, wherein the sheet member is constructed from an opaque material.

23. A sterile ocular cover for an eye during surgery, comprising a sheet member including a body sized for placement over and in contact with the surface of the conjunctiva of the eye, a wicking portion, and a handle, the sheet member being made of a flexible and absorbent material, the body including a hole therethrough, the hole being a diameter of 11–12 mm plus no more than about 6 mm larger than the hole diameter, the wicking portion extending outwardly from the body and being positionable over and in contact with a lateral canthus of the eye, the handle extending outwardly from the body and being positionable beyond the canthus of the eye, wherein the sheet member is impregnated with an antiseptic.

24. A sterile ocular cover for an eye during surgery, comprising a sheet member including a body sized for placement over and in contact with the surface of the conjunctiva of the eye, a wicking portion, and a handle, the sheet member being made of a flexible and absorbent material, the body including a hole therethrough, the hole being a diameter of 11–12 mm plus no more than about 6 mm larger than the hole diameter, the wicking portion extending outwardly from the body and being positionable over and in contact with a lateral canthus of the eye, the handle extending outwardly from the body and being positionable beyond the canthus of the eye, wherein the sheet member is impregnated with an antibiotic.

* * * * *